United States Patent [19]

Lachhein et al.

[11] Patent Number: 5,208,337

[45] Date of Patent: May 4, 1993

[54] PROCESS FOR THE PREPARATION OF AMINOPYRIMIDINES

[75] Inventors: Stephen Lachhein, Hofheim am Taunus; Hilmar Mildenberger, Kelkheim (Taunus), both of Fed. Rep. of Germany

[73] Assignee: Hoechst Aktiengesellschaft, Frankfurt am Main, Fed. Rep. of Germany

[21] Appl. No.: 759,898

[22] Filed: Sep. 13, 1991

[30] Foreign Application Priority Data

Sep. 15, 1990 [EP] European Pat. Off. ........ 90117823.6

[51] Int. Cl.$^5$ ............................................. C07D 239/42
[52] U.S. Cl. ................................................... 544/320
[58] Field of Search ........................................ 544/320

[56] References Cited

U.S. PATENT DOCUMENTS 4,169,719 10/1979 Levitt ....................................... 71/92
4,831,138 5/1989 Lacchein ............................ 544/320

FOREIGN PATENT DOCUMENTS 0024200 8/1980 European Pat. Off. .
0071958 2/1983 European Pat. Off. .
0271834 12/1987 European Pat. Off. .
0424849 10/1990 European Pat. Off. .
2426913 12/1975 Fed. Rep. of Germany .

OTHER PUBLICATIONS

Roger et al., Chem. Rev. 61, 179 (1961).
McElvain et al., JACS 71 40 (1949).

*Primary Examiner*—John M. Ford
*Attorney, Agent, or Firm*—Curtis, Morris & Safford

[57] ABSTRACT

2-Aminopyrimidines of the formula I

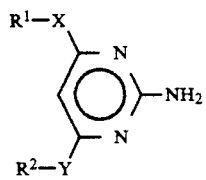

in which X and Y are O or S and $R^1$ and $R^2$ independently of one another are lower alkyl, alkoxyalkyl or haloalkyl, are obtained by reacting propanediimidates of the formula II $$R^1-X-C(=NH)-CH_2-C(=NH)-Y-R^2 \quad (II)$$

or salts thereof with cyanamide in the presence of a base at pH values above pH 7.

The process allows the aminopyrimidines to be prepared in a one-pot reaction

10 Claims, No Drawings

PROCESS FOR THE PREPARATION OF AMINOPYRIMIDINES

DESCRIPTION

The invention relates to a process for the preparation of pyrimidines of the formula I

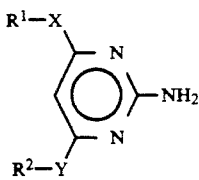

in which X and Y in each case are oxygen or sulfur and $R^1$ and $R^2$ independently of one another are $(C_1-C_4)$alkyl, $(C_1-C_4)$alkoxy$(C_1-C_2)$alkyl or halo$(C_1-C_4)$alkyl, by reacting a propanediimidate of the formula II

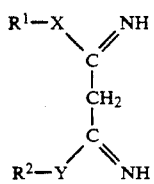

or a salt thereof with cyanamide ($NH_2$—CN) in the presence of a base, which comprises adding the propanediimidate or its salt to a solution of a base and cyanamide in an inert solvent at pH values of above pH 7 to pH 14 and carrying out the reaction.

Compounds of the formula I are valuable intermediates in the preparation of sulfonylureas which have herbicidal action (U.S. Pat. No. 4,169,719, EP-A 071,958 (U.S. Pat. No. 4,492,598)).

It is known that pyrimidines of the formula I can be prepared by reacting the propanediimidates with an aqueous cyanamide solution (EP-A 0,024,200).

This process is characterized by a multi-step reaction sequence in which 1) the compound of the formula II is reacted with bases,
2) the product is reacted with cyanamide to form an intermediate which can be isolated, and
3) the product is cyclized to give compounds of the formula I.

A particular disadvantage here is the fact that the reaction must be carried out in a narrow pH range (pH 5-7). Apart from presenting operational problems, the propanediimidate, or its di- or monosalt, which acts as starting substance, undergoes hydrolysis reactions in the acid aqueous solution (R. Rogers and D. G. Neilson, Chem. Reviews, 61, p. 179, 1961). This causes the formation of a substantial amount of secondary products, which results in unsatisfactory purity levels and yields in the end products.

In contrast, the process according to the invention surprisingly presents an operationally simple single- or two-step process without intermediates which can be isolated, this process allowing the reaction to be carried out as a one-pot process without particular pH monitoring. Secondary products are only formed to an insignificant extent.

An increase of this kind in the yield and purity of the end products was not to be expected on the basis of increasing the pH to values above 7 and the direct contact of all starting materials (propanediimidate, cyanamide and base).

The process according to the invention is expediently carried out in such a manner that the propanediimidate in the form of a salt, for example a dihydrochloride salt, is added to a solution of base and cyanamide in an inert solvent at reaction temperatures from $-20°$ to $200°$ C., preferably $-10°$ to $150°$ C., and a pH of above 7, preferably 7.1 to 12, in particular 8 to 11, and the reaction is carried out. The solution of base and cyanamide preferably contains at least 1 equivalent of base and at least 1 mol of cyanamide per mol of propanediimidate employed. A small excess of base, for example up to 10%, is particularly preferred. This ensures that the pH remains above 7 during the entire reaction time.

The propanediimidate salts employed are preferably those of hydrofluoric, hydrochloric or hydrobromic acid, of sulfuric acid or of phosphoric acid. Haloalkyl radicals for $R^1$ and $R^2$ are, for example, $CH_2CH_2Cl$ or $CH_2CF_3$. X and Y are in each case preferably oxygen; $R^1$ and $R^2$ are in each case preferably $(C_1-C_4)$alkyl, in particular methyl.

Inert solvents which can be used are water, alcohols such as methanol, ethanol and propanol; ketones such as acetone and methyl isobutyl ketone; ethers such as diethyl ether, dioxane and tetrahydrofuran; esters such as methyl acetate, ethyl acetate and butyl acetate; hydrocarbons such as toluene, xylene and cyclohexane; nitriles such as acetonitrile and halogenated hydrocarbons such as dichloromethane or chloroform, or mixtures of these.

Examples of bases which can be used are the hydroxides, carbonates, hydrogen carbonates or alcoholates of alkali metals and alkaline earth metals.

To avoid oxygen interfering with the reaction, it is advantageous to carry out the process under an inert gas atmosphere, for example under nitrogen.

The compounds of the formula II can be prepared by known methods (S. M. McElvain and I. D. Schroeder, J. Am. Chem. Soc. 71, 40 (1949); B. Harstun, DE-A 2,426,913).

The examples which follow are intended to illustrate the process according to the invention in greater detail:

EXAMPLE 1

A solution is prepared of 50 g of potassium hydrogen carbonate, 250 ml of water and 27.3 g of cyanamide, the pH is adjusted to 8.5, and 101.5 g of dimethylpropanediimidate dihydrochloride are added under nitrogen. Stirring is continued for 4 hours, and the solid which has precipitated is filtered off with suction and heated on a water separator in 400 ml of toluene. The resulting solution is filtered while hot, and the solvent is removed in vacuo. There remain 69.7 g of product, 2-amino-4,6-dimethoxypyrimidine, of a purity of 99.4%, which corresponds to a yield of 90% of theory. The melting point is 93°-95° C.

EXAMPLE 2

25 g of potassium hydrogen carbonate, 75 ml of water, 13.6 g of cyanamide and 200 ml of methyl isobutyl ketone are combined and the mixture is cooled to 0° C. A pH of 8.5 is established. To this solution there are added 50.8 g of dimethyl propanediimidate dihydrochloride, and stirring is continued for 4 hours. The solution is heated to 100° C., filtered while hot, and refluxed for a further 2 hours. After the solvent has been removed in vacuo, there are obtained 34.7 of 2-amino-4,6-dimethoxypyrimidine of a purity of 98.2% which corresponds to a yield of 89.8% of theory.

EXAMPLE 3

At a pH of above 7 and a temperature of 0° C., 27 g of sodium methylate in 250 ml of methanol and 21 g of cyanamide are treated with 101.5 g of dimethyl propanediimidate dihydrochloride. The mixture is stirred for 4 hours at room temperature, and the salt is filtered off, and the solvent is distilled of using xylene. There remain 68.9 g of 2-amino-4,6-dimethoxypyrimidine of a purity of 98.4%, which corresponds to a yield of 89.4% of theory.

EXAMPLE 4 (WITHOUT NITROGEN AS PROTECTIVE GAS)

A solution of 50 g of potassium hydrogen carbonate, 312.5 ml of water and 27.3 f cyanamide is adjusted to pH 8.5, and, at 0° C., 101.5 g of dimethyl propanediimidate dihydrochloride are added. Stirring is continued for 4 hours, and precipitated solid is then filtered off with suction, and the product is heated in a water separator in 400 ml of toluene. The resulting solution is filtered while hot, and the solvent is removed in vacuo. There remain 69.4 g of product, 2-amino-4,6-dimethoxypyrimidine, in a purity of 99.1%, which corresponds to a yield of 89.3% of theory. The melting point is 93°–95° C.

COMPARISON EXAMPLE 1 (BY THE METHOD IN EP-A 0,024,200)

62 g of sodium hydrogen carbonate are dissolved in 600 ml of water, and, at 0° C. and a pH of 5 to 7, treated with 50 g of dimethyl propanediimidate dihydrochloride. When the latter has dissolved completely, 65 g of a 50% cyanamide solution are added. The mixture is stirred for 2 hours at room temperature, the precipitate is filtered off with suction, the aqueous phase is extracted once with methylene chloride, and the solvent is removed in vacuo. This gave 82.4 g of 3-amino-3-methoxy-N-cyano-2-propeneimidate, which was refluxed for 2 hours with 1000 ml of toluene. After the solvent has been removed, there remain 79.8 g of product of a purity of 95.8%, which corresponds to a yield of 71.3% of theory. The melting point is 92°–94° C.

COMPARISON EXAMPLE 2 (BY THE METHOD IN EP-A 0,024,200)

62 g of sodium hydrogen carbonate are dissolved in 600 ml of water and, at 0° C. and a pH of 5–7, treated with 150 g of dimethyl propanediimidate dihydrochloride. When the latter has dissolved completely, 92 g of a 50% cyanamide solution are added. The mixture is stirred for 3 hours, solids are filtered off with suction, and the mixture is refluxed for 2 hours with 1000 ml of toluene. After the solvent has been removed, there remain 76.0 g of product of a purity of 94.8%, which corresponds to a yield of 67.2% of theory. The melting point is 92°–94° C.

Other compounds of the formula I which can be prepared analogously to the procedures described in Examples 1–3 are, for example, the following:

| Example | X | Y | $R^1$ | $R^2$ |
|---|---|---|---|---|
| 4 | O | O | $C_2H_5$ | $C_2H_5$ |
| 5 | O | O | CH—$CH_3$ $CH_3$ | CH—$CH_3$ $CH_3$ |
| 6 | S | S | $CH_3$ | $CH_3$ |
| 7 | S | S | $C_2H_5$ | $C_2H_5$ |
| 8 | S | S | CH—$CH_3$ $CH_3$ | CH—$CH_3$ $CH_3$ |
| 9 | O | O | $CH_2$—$CH_2$—$OCH_3$ | $CH_2$—$CH_2$—$OCH_3$ |
| 10 | O | O | $CF_2H$ | $CF_2H$ |
| 11 | O | O | $CH_2CF_3$ | $CH_2CF_3$ |
| 12 | O | O | $CH_2FCF_2H$ | $CH_2FCF_2H$ |
| 13 | O | O | $CH_2CH_2Cl$ | $CH_2CH_2Cl$ |

We claim:
1. A process for the preparation of compounds of the formula I

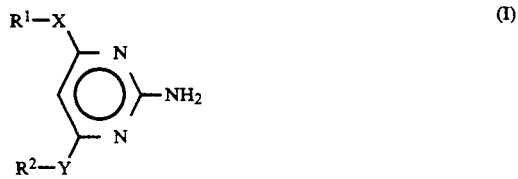

in which X and Y are in each case oxygen or sulfur and $R^1$ and $R^2$ independently of one another are ($C_1$-$C_4$)alkyl, ($C_1$-$C_4$)alkoxy($C_1$-$C_2$)alkyl or halo($C_1$-$C_4$)alkyl, by reacting a propanediimidate of the formula II

or a salt thereof with cyanamide ($NH_2$—CN) in the presence of a base, which comprises adding the propanediimidate or its salt to a solution of a base and cyanamide in an inert solvent at pH values of above pH 7 to pH 14 and carrying out the reaction.

2. The process as claimed in claim 1, wherein the reaction is carried out at pH values from 7.1–12.

3. The process as claimed in claim 2, wherein the pH is 8 to 11.

4. The process as claimed in claim 1, wherein, in formula I, X and Y in each case are an oxygen atom and $R^1$ and $R^2$ in each case are ($C_1$-$C_4$)alkyl.

5. The process as claimed in claim 4, wherein $R^1$ and $R^2$ are in each case methyl.

6. The process as claimed in claim 1, wherein water, an alcohol, a ketone, a hydrocarbon, a halogenated hydrocarbon, an ether, an ester, a nitrile or mixtures of these are used as inert solvent.

7. The process as claimed in claim 1, wherein salts of hydrofluoric acid, hydrochloric acid or hydrobromic acid, of sulfuric acid or of phosphoric acid, are used as salts of the compound of the formula II.

8. The process as claimed in claim 1, wherein the reaction temperatures are from −20° C. to 200° C.

9. The process as claimed in claim 1, wherein the reaction temperatures are from −10° C. to 150° C.

10. The process as claimed in claim 1, which comprises adding the compound of the formula II or a salt thereof to a solution which contains at least 1 equivalent of base and at least 1 ml of cyanamide per mol of compound of the formula II, and carrying out the reaction.

* * * * *